(12) United States Patent
Rossi et al.

(10) Patent No.: US 9,212,363 B2
(45) Date of Patent: Dec. 15, 2015

(54) RNAI MOLECULES WITH NON-WATSON CRICK PAIRING BASED ON ARTIFICIAL MUTATION CONSENSUS SEQUENCES TO COUNTER ESCAPE MUTATIONS

(71) Applicant: CITY OF HOPE, Duarte, CA (US)

(72) Inventors: John J. Rossi, Duarte, CA (US); Ulrike Jung, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 95 days.

(21) Appl. No.: 13/842,977

(22) Filed: Mar. 15, 2013

(65) Prior Publication Data

US 2013/0303589 A1  Nov. 14, 2013

Related U.S. Application Data

(60) Provisional application No. 61/646,181, filed on May 11, 2012.

(51) Int. Cl.
*C07H 21/04* (2006.01)
*C12N 15/113* (2010.01)

(52) U.S. Cl.
CPC ........ *C12N 15/1132* (2013.01); *C12N 15/1131* (2013.01); *C12N 2310/533* (2013.01); *C12N 2320/34* (2013.01)

(58) Field of Classification Search
CPC .................. C12N 15/1132; C12N 2310/533; C12N 2310/14
See application file for complete search history.

(56) References Cited

U.S. PATENT DOCUMENTS

| | | | |
|---|---|---|---|
| 7,365,058 B2 * | 4/2008 | Stoffel et al. ............. | 514/44 A |
| 8,008,472 B2 * | 8/2011 | McSwiggen et al. ........ | 536/24.5 |
| 8,329,892 B2 * | 12/2012 | Zamore et al. ............. | 536/25.3 |
| 2006/0211642 A1 * | 9/2006 | McSwiggen et al. ........... | 514/44 |
| 2008/0318210 A1 * | 12/2008 | Bentwich ........................ | 435/6 |
| 2009/0192103 A1 * | 7/2009 | Rivory et al. ................. | 514/44 |

FOREIGN PATENT DOCUMENTS

JP  2008306962 A  *  6/2009

OTHER PUBLICATIONS

Yeung et al. Cell Research 15:935-946, 2005.*
English Translation of JP2008306962A published Jun. 18, 2009, pp. 1-33.*
Anderson, A. C., R. H. O'Neil, et al. (1999). "Crystal structure of a brominated RNA helix with four mismatched base pairs: An investigation into RNA conformational variability." Biochemistry 38(39): 12577-12585.
Bao, Y., P. Bolotov, et al. (2008). "The influenza virus resource at the National Center for Biotechnology Information." J Virol 82(2): 596-601.
Boghaert, E. et al. (2004). "Antibody-Targeted Chemotherapy with the Calicheamicin Conjugate hu3S193-N-Acetyl γ Calicheamicin Dimethyl Hydrazide Targets Lewis y and Eliminates Lewis y-Positive Human Carcinoma Cells and Xenografts." Clinical Cancer Res 10:4538-4549.
Du, G., J. Yonekubo, et al. (2006). "Design of expression vectors for RNA interference based on miRNAs and RNA splicing." FEBS J 273(23): 5421-5427.
Du, Q., H. Thonberg, et al. (2005). "A systematic analysis of the silencing effects of an active siRNA at all single-nucleotide mismatched target sites." Nucleic Acids Res 33(5): 1671-1677.
Holen, T., S. E. Moe, et al. (2005). "Tolerated wobble mutations in siRNAs decrease specificity, but can enhance activity in vivo." Nucleic Acids Res 33(15): 4704-4710.
Joseph, T. T. and R. Osman (2012). "Convergent transmission of RNAi guide-target mismatch information across Argonaute internal allosteric network." PLoS Comput Biol 8(9): e1002693.
Sun, H., J. Sheng, et al. (2012). "Novel RNA base pair with higher specificity using single selenium atom." Nucleic Acids Res., pp. 5171-5179.
Vendeix, F. A., F. V. t. Murphy, et al. (2012). "Human tRNA(Lys3)(UUU) is pre-structured by natural modifications for cognate and wobble codon binding through keto-enol tautomerism." J Mol Biol 416(4): 467-485.
Westerhout, E. M., M. Ooms, et al. (2005). "HIV-1 can escape from RNA interference by evolving an alternative structure in its RNA genome." Nucleic Acids Res 33(2): 796-804.

* cited by examiner

*Primary Examiner* — Brian Whiteman
(74) *Attorney, Agent, or Firm* — Perkins Coie LLP; Lara Dueppen

(57) ABSTRACT

Universal RNA interference (RNAi) molecules having an inhibitory RNA sequence which binds a target pathologic RNA sequence are provided according to some embodiments. Such RNAi molecules bind the target pathologic RNA sequence via at least one non-Watson Crick paired base. In some embodiments, the target pathologic RNA sequence is a target viral RNA sequence derived from a human immunodeficiency HIV virus, a hepatitis B virus (HBV), a hepatitis C virus (HCV), or an influenza virus.

3 Claims, 11 Drawing Sheets

| region 4 | mRNA complement 5' - 3' | |
|---|---|---|
| | original strain | TAATACTGTATCATCTGCTCCTGT (SEQ ID NO: 40) |
| | mutation outside | TAATACTGTATCATCTGCTCCTGT (SEQ ID NO: 40) |
| | mutation inside R4 | TAATACTGTATCATCTGCTCCgGT (SEQ ID NO: 41) |

| | MuSTER 5' - 3' | |
|---|---|---|
| | R4-1 gains new nonWCp at nt 19 | UACUGUAUCAUCUGCUCCuGU (SEQ ID NO: 29) |
| | R4-2 unaffected | UAGUACUGUAUCAUCUGCUCC (SEQ ID NO: 31) |
| | R4-3 gains new nonWCp at nt 20 | GUACUGUAUCAUCUGCUCCuG (SEQ ID NO: 33) |
| | R4-4 gains new nonWCp at nt 21 | AGUACUGUAUCAUCUGCUCCu (SEQ ID NO: 35) |
| | | nonWCp ... non-Watson-Crick pairing |

| region 3 | mRNA complement 5' - 3' | |
|---|---|---|
| | original strain | CCTACATACAAATCATCCATGTATTGATA (SEQ ID NO: 42) |
| | mutation outside | CCTACATACAAATCATCCATGTATTGATA (SEQ ID NO: 42) |
| | mutation inside R4 | CCTACATACAAATCATCCATGTATTGATA (SEQ ID NO: 42) |

| | MuSTER 5' - 3' | |
|---|---|---|
| | R3-2 unaffected | UAGGUCGUCCAUGUAUUGGUA (SEQ ID NO: 25) |
| | R3-3 unaffected | UAUAGGUCGUCCAUGUAUUGG (SEQ ID NO: 27) |

Fig. 10

RNAI MOLECULES WITH NON-WATSON CRICK PAIRING BASED ON ARTIFICIAL MUTATION CONSENSUS SEQUENCES TO COUNTER ESCAPE MUTATIONS

PRIORITY CLAIM

This application claims priority of U.S. Provisional Application No. 61/646,181, filed May 11, 2012, the subject matter of which is hereby incorporated by reference as if fully set forth herein.

STATEMENT OF GOVERNMENT INTEREST

The present invention was made with government support under Grant Nos. HL07470, AI39239/ and AI42552, awarded by the National Institutes of Health. The Government has certain rights in the invention.

BACKGROUND

RNA interference (RNAi) is a mechanism endogenously existing in cells to suppress the expression of genes through interaction of protein complexes with the mRNA. Naturally occurring RNAi relies on microRNAs. MicroRNAs (miRNA) are processed from RNAs sequences that fold into an internal stem-loop structure. 5' and 3' adjacent sequences are cut off as well as the loop leaving a short double stranded RNA with usually 2 nucleotides overhangs on the 3' end of each strand. One of the strands is degraded while the other strand remains (the guide strand). The guide strand is incorporated into a protein complex leading to degradation or translational repression of mRNA targets, which are at least partially complementary. The mechanism of RNAi has been artificially employed since several years now by the introduction of shRNA stem-loop sequences that are processed like miRNA but due to full complementarity with the target mRNA always leads to its degradation. And there are siRNAs that are used as triggers of RNAi, which are already fully processed miRNA but usually contain full complementary strands and show full complementarity with the target RNA the same as processed shRNAs.

RNAi based therapy is very appealing due to its target specificity at very low doses, which can avoid common drug intrinsic side effects. Furthermore, in case of long term treatment like gene therapy RNAs have the advantage to be not prone to immune response while proteins are.

However, current siRNAs and shRNAs (collectively, "si/shRNAs") targeting mammalian genes or pathologic mRNAs (like viruses for example) are designed based on actual sequences occurring in nature. In case of viruses that mutate the design, it relies on the identification of conserved regions in naturally available strain sequences. But, even conserved regions are not without mutations and the therapeutic pressure of therapeutic si/shRNAs readily leads to escape variants which render these si/shRNAs ineffective. Prime examples to generate escape strains are Human Immunodeficiency virus (HIV), Hepatitis C virus (HCV) and Hepatitis B virus (HBV). Therefore, it would be desired to generate universal RNA interference molecules that would retain their efficacy when such viruses mutate.

SUMMARY

Universal RNA interference (RNAi) molecules having an inhibitory RNA sequence which binds a target pathologic RNA sequence are provided herein. In some embodiments, the RNAi molecules bind the target pathologic RNA sequence via at least one non-Watson Crick paired base. In some embodiments, the target pathologic RNA sequence is a target viral RNA sequence derived from a human immunodeficiency HIV virus, a hepatitis B virus (HBV), a hepatitis C virus (HCV), or an influenza virus.

In some embodiments, methods for treating a subject infected with a target virus are provided. Such embodiments include a step of administering a therapeutically effective amount of an RNAi molecule to the subject, wherein the RNAi molecule includes an inhibitory RNA sequence which binds a target viral RNA sequence. In some aspects, the inhibitory RNA sequence binds the target viral RNA sequence via at least one non-Watson Crick paired base.

In some embodiments, the target viral RNA sequence derived from a human immunodeficiency HIV virus. In such embodiments, the target viral RNA sequence may include an IUPAC sequence of URYCARUAYAUGGAYGAYYURUAUGURGG (SEQ ID NO:1) or YURGAYACRGGRGCAGAUGAUACAGUR (SEQ ID NO:2). In some aspects, the inhibitory RNA sequence may include an IUPAC or nucleotide sequence of YARRTCRTCCATRTAYTGRYA (SEQ ID NO:3); TAYARRTCRTCCATRTAYTGR (SEQ ID NO:4); TAGGTCGTCCATGTATTGGTA (SEQ ID NO:5); TATAGGTCGTCCATGTATTGG (SEQ ID NO:6); YACTGTATCATCTGCYCCYGT (SEQ ID NO:7); YADYACTGTATCATCTGCYCC (SEQ ID NO:8); DYACTGTATCATCTGCYCCYG (SEQ ID NO:9); ADYACTGTATCATCTGCYCCY (SEQ ID NO:10); TACTGTATCATCTGCTCCTGT (SEQ ID NO:11); TAGTACTGTATCATCTGCTCC (SEQ ID NO:12); GTACTGTATCATCTGCTCCTG (SEQ ID NO:13); or AGTACTGTATCATCTGCTCCT (SEQ ID NO:14).

In some embodiments, a method of designing an RNAi molecule may include steps including generating an inhibitory RNA sequence by generating a consensus sequence derived from two or more target pathologic RNA sequences; converting the consensus sequence into an International Union of Pure and Applied Chemistry (IUPAC) sequence code; substituting each ambiguous base with a base that allows for both Watson-Crick and non-Watson-Crick pairings; and selecting one or more inhibitory RNA molecules using an RNAi binding prediction algorithm. In some aspects, the consensus sequence is derived from a plurality of clinical isolates.

BRIEF DESCRIPTION OF THE DRAWINGS

FIG. 1 shows the origin of HIV subtypes and subtype composition selected for development of IUPAC artificial mutant sequence. 54 strains were selected from the most densely populated or geographically widely distributed areas in the world (shaded countries) to cover as many HIV-1 subtypes as possible and to ensure maximum strain variance. Several subtypes are represented in the selected strains, which are as indicated.

FIG. 2 shows knockdown of Renilla luciferase normalized to Firefly luciferase in psiCheck2.1 constructs with 1056 nucleotides of integrated gag-pol region FIG. 3 shows transfection control between different samples. Firefly absolute values 48 hours after transfection vary little and show no correlation with the knockdown values obtained. Mean of technical triplicate with average deviation.

FIG. 4 shows a standard curve p24 assay.

FIG. 5 shows p24 Levels relative to sample transfected just with empty (no shRNA) construct. HIfB cells were transfected with Lipofectamine 2000 and each sample received 100 ng pCMV-rev plasmid and 700 ng of a plasmid mix containing 338 ng shRNA or empty construct (a) with the remainder comprised of empty construct or 26 ng shRNA or empty construct (b) with the remainder comprised of empty construct.

FIG. 6: p24 Levels relative to sample transfected just with empty (no shRNA) construct. HEK293T cells were transfected with Lipofectamine 2000 and each sample received 200 ng pNL4-3 plasmid and 600 ng of a plasmid mix containing 338 ng shRNA or empty construct with the remainder comprised of empty construct.

FIG. 7 illustrates the activity of MuSTER and conventional shRNA (U6 driven or MuSTER intron background) in IIIB challenge of CEM-CCR5 cells stably transduced. Empty is vector without any anti-HIV shRNA.

FIG. 8 shows p24 levels in CEM-CCR5 cells transduced with lentiviral MuSTER-designed expression constructs and challenged with the HIV IIIB strain, normalized to an empty construct (day 8). S1 is a conventional anti-HIV from the same cassette or U6 promoter driven. MuSTER-designed shRNA constructs Mu3-2, Mu3-3, Mu4-1, Mu4-2, Mu4-3 and Mu4-4 are the same as, and correspond to, shRNA constructs R3-2, R3-3, R4-1, R4-2, R4-3 and R4-4 described herein.

FIG. 10 shows the details of the shRNA positions and binding regions of the constructs shown in FIG. 9.

Figure 11:
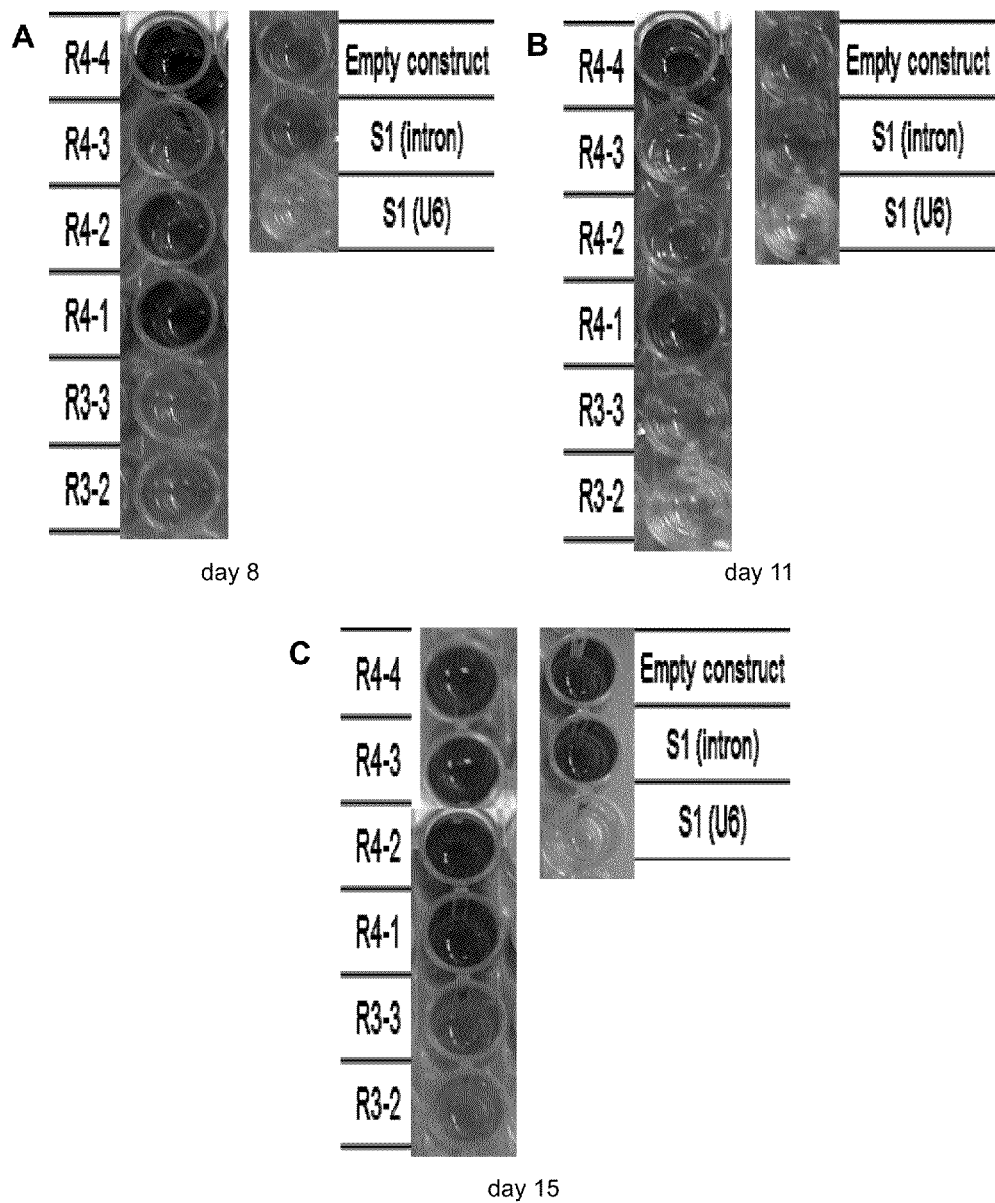

FIG. 11 shows a p24 photography assay at day 8 (A), day 11 (B) and day 15 (C) post challenged of CEM CCR5 cells with HIV IIIB. All samples diluted by 1:100.

DETAILED DESCRIPTION

Universal RNA interference (RNAi) molecules that suppress the expression of one or more pathologic molecules (i.e., molecules that are associated with a disease, infection or other condition) by binding a target pathologic RNA sequence via at least one non-Watson Crick paired base are provided herein. The vulnerability of common RNAi molecules such as siRNA and shRNA lies in the design based on a single natural target sequence—while the design rules generally allow only Watson-Crick pairing between guide strand and target. This makes current RNAi design protocols limited. Watson-Crick pairings are pairings between the bases Adenine and Uracil in RNA and Guanine and Cytosine. However, non-Watson Crick pairings which have different energetic and spatial properties are possible too and have been found in natural RNA. The most common of these is the pairing between Uracil and Guanine. Others exist which include the non-conventional base Inosine to allow pairings between Inosine & Uracil, Inosine & Adenine and Inosine & Cytosine as well as the Uracil-Cytosin 4-carbonyl-amino pairing which has almost the same structure like the Uracil-Guanine pairing (Anderson, O'Neil et al. 1999). Pairing between modified or artificial bases are possible as well and can lead to even more effective binding than with naturally occurring bases (Sun, Sheng et al. 2012; Vendeix, Murphy et al. 2012).

It has been shown that introducing non-Watson Crick pairing between si/shRNA and the target sequence can still lead to significant gene suppression, in some cases even increased effects in vivo compared to fully complementary sequences. Designing RNAi molecules using non-Watson Crick pairing makes it possible to develop therapeutic molecules that retain their therapeutic activity, even when a target undergoes mutations (e.g., escape mutations).

According to the embodiments described herein, an RNAi molecule may be any suitable type of RNAi molecule which, when delivered to a target cell, associates with a RISC complex and binds a target RNA sequence to suppress or silence the expression of one or more pathologic molecules in the target cell. Such RNAi molecules may include, but are not limited to, micro RNA (miRNA) molecules, small interfering RNA (sRNA) molecules, and short hairpin RNA (shRNA) molecules.

In some embodiments, an RNAi molecule may be designed to suppress any pathologic molecule that is prone to mutation or allelic diversity including, but not limited to, pathogenic proteins (i.e., viral proteins, bacterial proteins, fungal proteins, parasitic proteins, or any other microorganism protein), pathologic RNA molecules, such as miRNAs, tRNA, rRNA, and other non-coding RNA (ncRNA) molecules, and genetic variants or mutants of endogenous protein coding regions and/or regulatory regions (e.g., certain oncogenes that are mutated, overexpressed or underexpressed). In some embodiments, the RNAi molecules bind a viral RNA sequence via at least one non-Watson Crick paired base, thereby suppressing the expression of a viral protein. In some embodiments, the RNAi molecules are designed to suppress expression of a viral protein derived from a human immunodeficiency virus (HIV), an influenza virus (e.g, Influenzavirus A, Influenzavirus B, Influenzavirus C), hepatitis B virus (HBV), or hepatitis C virus (HCV). In some aspects, the RNAi molecules are designed to suppress expression of an HIV protein (e.g., docking glycoprotein gp120, transmembrane glycoprotein gp41, p7, capsid protein p24, nucleocapsid protein p7, matrix protein p17, transcriptional transactivators p16 and p14, Vif protein p23, p27, rev protein p19) that is expressed from one or more HIV genes or gene regions (e.g., gag, pol, gag-pol, env, rev, nef, vif, vpr, vpu, tev).

In some embodiments, the RNAi molecules provided herein may include an inhibitory RNA sequence that binds a target pathologic RNA sequence that may encode a pathologic protein or may itself be a noncoding RNA sequence, which may be designed using a method referred to herein as Multi-SubType Escape Reducing (MuSTER) design. A MuSTER design method may include a step of generating an inhibitory RNA sequence by generating a consensus sequence derived from two or more target pathologic RNA sequences. In some aspects, the target pathologic RNA sequence may be a consensus sequence that is generated from two or more target RNA sequences that encode two or more wild type or variant isotypes, escape variants, or mutants of the same protein, noncoding RNA or regulatory sequence. In some aspects, the two or more target RNA sequences are from a conserved sequence.

In certain embodiments, the target RNA sequences may be part of two or more viral genomes or nucleotide sequences (e.g., cDNA, or RNA) that are transcribed from the viral genome (i.e., nucleotide sequences that are a result of reverse transcription of an RNA virus or revrovirus or a result of transcription of the viral genome after integration with the host genome). In such embodiments, the MuSTER design method may include a step of generating an inhibitory RNA sequence by generating a consensus sequence from two or more clinical isolates. In this case, the two or more viral genomes may be derived from two or more clinical isolates. Clinical isolates are samples of a pathogen (e.g., virus, bacteria, or other microorganism) that are isolated from a biological sample of a subject infected with the pathogen, the sequences of which may be found on publicly available databases such as those found in Table 1 below. As such, in some embodiments, the two or more target RNA sequences that may be used to generate a consensus sequence for designing a universal RNAi molecule in accordance with the embodiments described herein may be derived from two or more sequences from clinical isolates found in one or more of the databases in Table 1.

TABLE 1

Viral sequence databases

| Virus | Database | Website |
|---|---|---|
| HIV-1 | Los Alamos HIV Database: | http://www.hiv.lanl.gov/content/sequence/HIV/mainpage.html |
| | Stanford HIV RT and Protease Sequence Database: | http://hivdb.stanford.edu |
| | NCBI/Genbank | http://www.ncbi.nlm.nih.gov/nuccore |
| HCV | Los Alamos HCV Database | http://hcv.lanl.gov/content/sequence/HCV/ToolsOutline.html |
| Influenza | NCBI Influenza Virus Resource (Bao, Bolotov et al. 2008) | http://www.ncbi.nlm.nih.gov/genomes/FLU/Database/nph-select.cgi?go=1 |

In some embodiments, the MuSTER method may then include a step of converting the consensus sequence into an International Union of Pure and Applied Chemistry (IUPAC) sequence code. The IUPAC sequence includes a nucleotide code that includes several degenerate nucleotide code letters that represent one or more possible alternative bases that may be used at a particular position. Nucleotide code letters that represent more than one possible alternative bases are also known as "ambiguous bases." Table 2 below shows the nucleotide code letters and corresponding base(s).

TABLE 2

IUPAC Sequence

| Nucleotide Code | Base |
|---|---|
| A | Adenine |
| C | Cytosine |
| G | Guanine |
| T (or U) | Thymine (or Uracil) |
| R | A or G |
| Y | C or T |
| S | G or C |
| W | A or T |
| K | G or T |
| M | A or C |
| B | C or G or T |
| D | A or G or T |
| H | A or C or T |
| V | A or C or G |
| N | any base |
| . or - | gap |

By converting the consensus sequence into an IUPAC sequence code, one can design a universal RNAi molecule that would bind one or more target pathologic RNA sequences that may differ by one or more nucleotides (i.e., the RNAi molecule may be used to bind one or more strains or variants of a particular target). The IUPAC sequence code is then transformed into a candidate RNAi molecule by substituting each ambiguous base with a base that allows for both Watson-Crick and non-Watson-Crick pairings: thymine (T) or uracil (U) is substituted with the IUPAC nucleotide code "R" to account for its Watson-Crick pairing base (A) or its non-Watson-Crick pairing base (G); and guanine (G) is substituted with the IUPAC nucleotide code "Y" to account for its Watson-Crick pairing base (C) or its non-Watson-Crick pairing base (T) or (U).

In some embodiments, the MuSTER method may also include a step of selecting one or more inhibitory RNA molecules using a suitable RNAi binding prediction algorithm. Suitable binding prediction algorithms are known in the art, and may include publicly and commercially available prediction tools including, but not limited to, DSir (http://biodev.extra.cea.fr/DSIR/DSIR.html) (Vert et al. 2006); siRNA at Whitehead (http://sirna.wi.mit.edu/); BLOCK-iT™ RNAi Designer at Life Technologies (http://rnaidesigner.invitrogen.com/rnaiexpress/); siDESIGN Center at Thermo Scientific (http://www.thermoscientificbio.com/design-center/); IDT SciTools RNAi Design at Integrated DNA Technologies (http://www.idtdna.com/scitools/applications/rnai/rna-i.aspx); and German Cancer Research Center E-RNAi (http://www.dkfz.de/signaling/cgi-bin/e-rnai3/settings.pl).

In one embodiment, the MuSTER method may produce an RNAi molecule (also referred to as "MuSTER RNAi," "MuSTER designed RNAi," or "MuSTER designed shRNA" or the like) that includes an inhibitory RNA sequence that suppresses a target pathologic RNA sequence that is derived from a retrovirus, such as an HIV virus, and HCV virus or an influenza virus. In such embodiments, the pathologic RNA sequence that is suppressed by the inhibitory molecule may be part of the retroviral genome or may be part of an mRNA sequence that is transcribed by the host after integration.

In certain embodiments, the inhibitory RNA sequence may bind to at least a portion of a target viral RNA sequence that is derived from an HIV virus or a consensus sequence that is derived from a plurality of HIV viral strains, variants or mutants (i.e., a "target viral RNA sequence"). In such embodiments, the target viral RNA sequence may include an IUPAC sequence of URYCARUAYAUGGAYGAYYURUAUGURGG (SEQ ID NO:1) or YURGAYACRGGRGCAGAUGAUACAGUR (SEQ ID NO:2). In one aspect, expression of the target viral RNA sequence URYCARUAYAUGGAYGAYYURUAUGURGG (SEQ ID NO:1) is suppressed by an inhibitory RNA sequence selected from YARRTCRTCCATRTAYTGRYA (SEQ ID NO:3); TAYARRTCRTCCATRTAYTGR (SEQ ID NO:4); TAGGTCGTCCATGTATTGGTA (SEQ ID NO:5); or TATAGGTCGTCCATGTATTGG (SEQ ID NO:6). In another aspect, expression of the target viral RNA sequence YURGAYACRGGRGCAGAUGAUACAGUR (SEQ ID NO:2) is suppressed by an inhibitory RNA sequence selected from YACTGTATCATCTGCYCCYGT (SEQ ID NO:7); YADYACTGTATCATCTGCYCC (SEQ ID NO:8); DYACTGTATCATCTGCYCCYG (SEQ ID NO:9); ADYACTGTATCATCTGCYCCY (SEQ ID NO:10); TACTGTATCATCTGCTCCTGT (SEQ ID NO:11); TAGTACTGTATCATCTGCTCC (SEQ ID NO:12); GTACTGTATCATCTGCTCCTG (SEQ ID NO:13); or AGTACTGTATCATCTGCTCCT (SEQ ID NO:14).

The inhibitory RNA sequences may be used as a pre-processed siRNA molecule or may be incorporated into an shRNA molecule which includes a passenger sequence and a guide sequence connected via a loop sequence. The passenger and guide sequences (or a pre-processed siRNA sequence) may be 18 nucleotides in length, 19 nucleotides in length, 20 nucleotides in length, 21 nucleotides in length, 22 nucleotides in length, 23 nucleotides in length, or any other suitable length. The loop sequence may be between 4 and 25 nucleotides in length, or any other suitable length. In some embodiments, the inhibitory RNA sequence may be selected from the following sequences in Table 3 below (passenger sequence is underlined, guide sequence is in bold, loop sequence is in italics):

TABLE 3

MuSTER designed shRNA sequences

| shRNA ID | shRNA encoding DNA template (5'-3') | Target viral RNA sequence (5'-3') |
|---|---|---|
| #3-2: | agcgATACCAATACATGGACGACCTA tagtgaagccacagatgtaTAGGTCGTCCA TGTATTGGTAgtgcc (SEQ ID NO: 15) | URYCARUAYAUGGAYGAYYUR UAUGURGG (SEQ ID NO: 1) |
| #3-3 | agcgGCCAATACATGGACGACCTATA tagtgaagccacagatgtaTATAGGTCGTC CATGTATTGGttgcc (SEQ ID NO: 16) | URYCARUAYAUGGAYGAYYUR UAUGURGG (SEQ ID NO: 1) |
| #4-1 | agcgAACAGGAGCAGATGATACAGTA tagtgaagccacagatgtaTACTGTATCAT CTGCTCCTGTgtgcc (SEQ ID NO: 17) | YURGAYACRGGRGCAGAUGAU ACAGUR (SEQ ID NO: 2) |
| #4-2 | agcgGGGAGCAGATGATACAGTACTA tagtgaagccacagatgtaTAGTACTGTAT CATCTGCTCCttgcc (SEQ ID NO: 18) | YURGAYACRGGRGCAGAUGAU ACAGUR (SEQ ID NO: 2) |
| #4-3 | agcgGCAGGAGCAGATGATACAGTAC tagtgaagccacagatgtaGTACTGTATC ATCTGCTCCTGttgcc (SEQ ID NO: 19) | YURGAYACRGGRGCAGAUGAU ACAGUR (SEQ ID NO: 2) |
| #4-4 | agcgAAGGAGCAGATGATACAGTACT tagtgaagccacagatgtaAGTACTGTATC ATCTGCTCCTgtgcc (SEQ ID NO: 20) | YURGAYACRGGRGCAGAUGAU ACAGUR (SEQ ID NO: 2) |

A lot of effort has been spent in the last decade to find anti-HIV RNAi molecules such as shRNAs and siRNAs for example for gene therapy as RNAs are not prone to immune response while proteins are. The practical utility is that previous shRNAs/siRNAs targeting pathogens were rendered ineffective by naturally occurring mutants hampering the applicability in therapy. By designing universal sh/siRNAs that can tolerate naturally occurring mutations, the problem of mutant escape from RNAi may be solved.

Since no cure against HIV has yet been discovered, but gene therapy is a very promising option, finding escape-proof sequences is highly desired. The same holds true for infections with HCV or HBV for example against which no effective cure exists while the incidence is on the rise.

Pharmaceutical Compositions

According to some embodiments, the RNAi molecules described herein may be part of a pharmaceutical composition. Such a pharmaceutical composition may include one or more RNAi molecules and a pharmaceutically acceptable carrier. In some embodiments, the pharmaceutical composition may include a single RNAi molecule that targets a first pathologic RNA sequence, or alternatively, may include one or more additional RNAi molecules that target a second pathologic RNA sequence, a third pathologic RNA sequence, or any number of additional pathologic RNA sequences.

A "pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. Such a carrier may comprise, for example, a liquid, solid, or semi-solid filler, solvent, surfactant, diluent, excipient, adjuvant, binder, buffer, dissolution aid, solvent, encapsulating material, sequestering agent, dispersing agent, preservative, lubricant, disintegrant, thickener, emulsifier, antimicrobial agent, antioxidant, stabilizing agent, coloring agent, or some combination thereof.

Each component of the carrier is "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) natural polymers such as gelatin, collagen, fibrin, fibrinogen, laminin, decorin, hyaluronan, alginate and chitosan; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as triethylene carbonate, ethyl oleate and ethyl laurate; (13) agar; (14) buffering agents, such as magnesium hydroxide and aluminum hydroxide; (15) alginic acid (or alginate); (16) pyrogen-free water; (17) isotonic saline; (18) Ringer's solution; (19) alcohol, such as ethyl alcohol and propane alcohol; (20) phosphate buffer solutions; (21) thermoplastics, such as polylactic acid, polyglycolic acid, (22) polyesters, such as polycaprolactone; (23) self-assembling peptides; and (24) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of RNAi molecules in these formulations can vary widely, and will be selected primarily based on fluid volumes, viscosities, organ size, body weight and the like in accordance with the particular mode of administration selected and the biological system's needs.

Methods of Treatment

In some embodiments, methods of treating a subject that is suffering from a disease or condition that is associated with one or more pathologic molecules that are prone to mutation or allelic diversity. Pathologic molecules that may be associated with a disease or conditions may include proteins, non-coding RNA sequences, or other nucleotide sequences. In one embodiment, the methods are directed to treatment of a subject that is infected with a target virus. Such methods include administering a therapeutically effective amount of an RNAi molecule or pharmaceutically composition thereof to the subject. According to some embodiments, the RNAi molecule includes an inhibitory RNA sequence which binds a target viral RNA sequence via at least one non-Watson-Crick paired base, such as those described in accordance with the embodiments described herein. The treatment may be used to treat any suitable viral infection including, but not limited to, human immunodeficiency virus (HIV), an influenza virus (e,g, Influenzavirus A, Influenzavirus B, Influenzavirus C), hepatitis B virus (HBV), or hepatitis C virus (HCV). In some embodiments, the treatment may be used to treat any strain or mutant version of such viral infection.

The treatment may include administration of one RNAi molecule or pharmaceutical composition thereof which binds one target viral RNA sequence, or may include administration of two or more RNAi molecules or a pharmaceutical composition thereof, wherein each RNAi molecule targets a different target viral RNA sequence. This combination or combinatory treatment may be administered to increase the effectiveness of the treatment.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. For example, a treatment with an RNAi molecule or pharmaceutical composition thereof may be used to treat an active viral infection in a subject by suppressing the expression of one or more viral proteins that are involved with viral replication, integration or assembly, thereby preventing the spread of the virus. The treatments described herein may be used in any suitable subject, including a human subject or any mammalian or avian subject that needs treatment in accordance with the methods described herein (e.g., dogs, cats, horses, rabbits, mice, rats, pigs, cows).

An RNAi molecule or pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration. In one embodiment, the RNAi molecule or pharmaceutical composition thereof is administered parenterally. A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

In some embodiments, the RNAi molecules may be administered with a pharmaceutically effective carrier that allows the RNAi molecules to be delivered locally or systemically to one or more target cells (i.e., virally infected cells) or target organs by one or more suitable RNAi delivery methods known in the art including, but not limited to, viral delivery, liposomal delivery, nanoparticle delivery, targeted delivery (e.g., using an antibody, aptamer or other targeting molecule to facilitate delivery), direct administration into target organs, systemic injection of naked RNAi molecules, and eukaryotic transcription plasmid delivery to produce shRNA inside of the target cells.

An RNAi molecule or a pharmaceutical composition thereof can be given to a subject in the form of formulations or preparations suitable for each administration route. The formulations useful in the methods of the invention include one or more RNAi molecules, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of an RNAi molecule which can be combined with a carrier material to produce a pharmaceutically effective dose will generally be that amount of an RNAi molecule which produces a therapeutic effect.

Methods of preparing these formulations or compositions include the step of bringing into association an RNAi molecule with one or more pharmaceutically acceptable carriers and, optionally, one or more accessory ingredients. In general, the formulations are prepared by uniformly and intimately bringing into association an RNAi molecule with liquid carriers, or finely divided solid carriers, or both.

Formulations suitable for parenteral administration comprise an RNAi molecule in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents, viscous agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In one embodiment of the invention, an RNAi molecule or pharmaceutical composition thereof is delivered to a disease or infection site in a therapeutically effective dose. A "therapeutically effective amount" or a "therapeutically effective dose" is an amount of an RNAi molecule that produces a desired therapeutic effect in a subject, such as preventing or treating a target condition or alleviating symptoms associated with the condition. The most effective results in terms of efficacy of treatment in a given subject will vary depending upon a variety of factors, including but not limited to the characteristics of the RNAi molecule, the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

As described above, regular si/shRNAs (small interfering/small hairpin RNAs) are typically designed by calculating active sequences based on a naturally existing target sequence in the standard 4-letter code. For this subtypes or sub-strains are analyzed for conserved regions, then the majority sequence inside these chosen and the si/shRNA designed. The resulting sequence pool is small and decreases with the mutagenicity of the target organism. Once the target mutates these conventional RNAs lose activity due to bulge formation (Joseph and Osman 2012). This plays a major role for loss of efficacy in the treatment of infectious diseases like HIV or other pathogens which are prone to mutation and thus therapeutic "escape." Furthermore infectious agents often exist in subtypes or sub-strains which already have a more or less distinctive genetic setup at infection time point. A general therapeutic RNAi approach thus needs to be able to cope with distinctive RNA sequences at onset of, as well as developing sequences during the infection. As described in the Examples below, the approach to the design of regulatory RNAs is, therefore, not based on a naturally occurring sequence. Instead, an artificial sequence is created from as many subtypes or sub-strains as possible found world wide. That information is then encoded in the IUPAC code which covers mutation information by addition of several more than the typical 4 base letters. The artificial sequence is then analyzed for their composition in terms of conserved sequences covering non-Watson-Crick pairing. This yields a sequence selection which would otherwise be excluded from conventional si/shRNA design. The IUPAC sequence is then converted into an artificial template strain that has the IUPAC encoded Y (U or C possible) and R (G or A possible) positions replaced with the corresponding non-Watson-Crick pairing (G can pair with C or U, U can pair with A or G). Based on that artificial sequence the si/shRNAs are selected. Resulting predictions are reviewed for Non-Watson-Crick positions in the seed region (disfavoring of non-Watson crick in 2.-8. nucleotide from the 5' end of the guide strand to avoid off target pairing and positions 10 & 11 to avoid slicing blockage) and frequency (avoid non-Watson crick pairing next to each other and more than 4 in one sequence). These si/shRNAs are referred to as MuSTER si/shRNAs (Multi-SubType Escape Reducing) or MuSTER designed si/shRNAs. The results in an dual luciferase assays (HEK 293T), an HIV HXB2 integrated infection deficient pro-virus packaging (HeLa cells), replication competent NL4-3 packaging assay (HEK 293T cells) and a long term virus propagation assay with HIV IIIB (CEM CCR5 T cell line) demonstrate a high activity of the MuSTER design.

Example 1

Design of Constructs

Since non-Watson Crick pairs allow a single si/shRNA to cover several variants of target mRNA it could be used to generate mutation resistant RNAi. This would allow overcoming the current limitation of the RNAi method in therapy.

Figure 1:
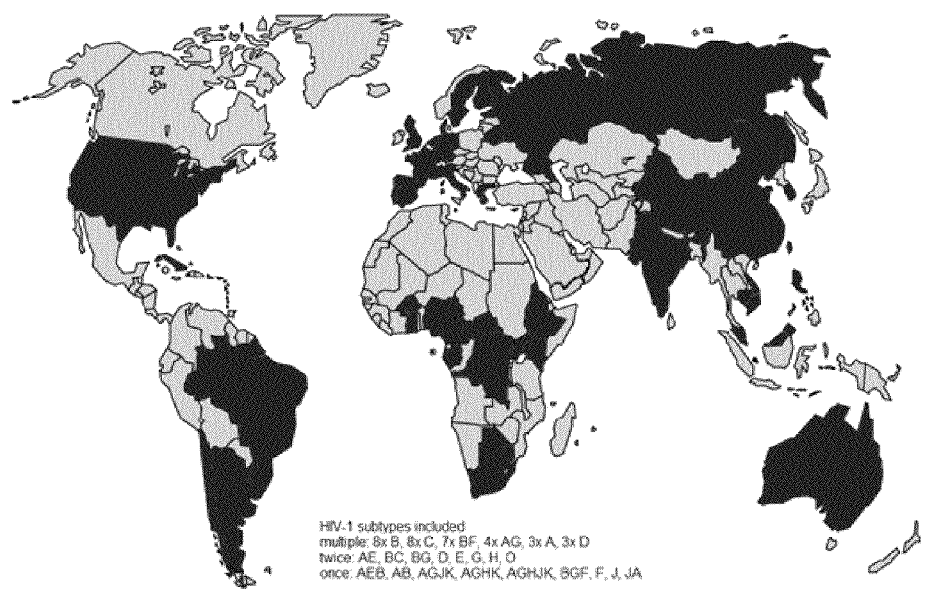

To test this, we generated for HIV an artificial consensus sequence of 54 different clinical isolates found world wide (FIG. 1), the sequences available at NCBI. This artifical sequence was encoded in IUPAC code, which contains a letter for ambiguous bases depending on the mutations occurring at each position. As next step every stretch was extracted that contained only the letters for bases Adenine, Guanine, Cytosine and Uracil (A, G, C, U) and the ambiguous letters for Cytosine or Uracil (pairing with Guanine, letter Y) and Guanine or Adenine (pairing with Uracil, letter R). These stretches would be conserved while targeted by fully complementary (including non-Watson Crick pairing) si/shRNAs. For all of these naturally occurring HIV subtypes no conventional si/shRNA was possible to design due to too high mutation rate of the virus. But several stretches of which were at least 22 nucleotides length the could be covered by MuSTER si/shRNAs were found and the resulting potential target sites are shown in Table 4 below

TABLE 4

Target sequences (IUPAC)

| Target Sequence | Length (nt) | Region of gag-pol | SEQ ID NO |
|---|---|---|---|
| ARRUGGAGRAARYURGURGAY UUYAGRGARYU | 32 | region 1 | 21 |
| URYCARUAYAUGGAYGAYYUR UAUGURGG | 29 | region 3 | 1 |
| RAUGAYAUCACARAARYURGU RGGRAAR | 28 | region 2 | 22 |
| YURGAYACRGGRGCAGAUGAU ACAGUR | 27 | region 4 | 2 |

TABLE 4 -continued

Target sequences (IUPAC)

| Target Sequence | Length (nt) | Region of gag-pol | SEQ ID NO |
|---|---|---|---|
| AARARRGGYUGYURGAARUGUR | 22 | region 5 | 23 |
| RRGGGARRRAGAURRGUGCRAG | 22 | region 6 | 24 |

Each of these sequences was transformed into an artificial DNA sequence where the ambiguous bases were replaced by a base that allowed both Watson-Crick and non-Watson Crick pairings (Thymine, the DNA analogue of Uracil for letter R and Guanine for letter Y). These artificial sequences were analyzed by the shRNA prediction tool DSir (available online) for effective si/shRNAs. As parameter, a length of 21 nucleotides (the longest prediction possible with DSir) with siRNA prediction was chosen. Predictions with highly ranked scores (above score of 75) were selected and analyzed for the position of the non-Watson Crick pairing bases. Every prediction which had a wobble at position 8-12 from the 3' end of the guide strand was excluded as previous reports indicated these would interfere with the siRNA activity.

The remaining 6 sequences predicted to be effective si/shRNAs were extended by one nucleotide on the 5' end of the guide strand (full complementarity to the target strand) and the resulting 22 nucleotide long sequences placed into human pre-microRNA 30 based backbones as described in (Du, Yonekubo et al. 2006). The resulting designs are shown in Table 3 above.

These would be processed into sequences that align as follows ("3' IUPAC" represents the complementary sequence to the target RNA sequence; "5' as RNA" represents the guide sequence of the shRNA or the inhibitory RNA sequence; and "3' mRNA majority" represents the mRNA target viral RNA sequence):

```
REGION 3 IUPAC Target RNA Sequence:

TRYCARTAYATGGAYGAYYTRTATGTRGG (SEQ ID NO: 36)

shRNA #3-2 (UR3-2 21nt DSir: 93.9 score)

3' IUPAC            YARRTCRTCCATRTAYTGRYA (SEQ ID NO:  3)

5' as RNA           UAGGUCGUCCAUGUAUUGGUA (SEQ ID NO: 25)
                    ||~~||~|||||||||||~||
3' mRNA majority    GTTTAGTAGGTACATAACTAT (SEQ ID NO: 26)

Wobble position (~) 3,4,7,19-> favored for no or beneficial effect shRNA #3-3 (UR3-3 21nt DSir: 91.4 score)

3' IUPAC            TAYARRTCRTCCATRTAYTGR (SEQ ID NO:  4)

5' as RNA           UAUAGGUCGUCCAUGUAUUGG (SEQ ID NO: 27)
                    ||~|~~||~|||||||||||~
3' mRNA majority    ATGTTTAGTAGGTACATAACT (SEQ ID NO: 28)

Wobble position (~) 3,5,6,21-> favored for no or beneficial effect, 9-> probably disfavored REGION 4 IUPAC Target RNA Sequence:

YTRGAYACRGGRGCAGATGATACAGTR (SEQ ID NO: 37)

shRNA #4-1 (UR4-1 21nt DSir: 92.6 score)

3' IUPAC            YACTGTATCATCTGCYCCYGT (SEQ ID NO:  7)

5' as RNA           UACUGUAUCAUCUGCUCCUGU (SEQ ID NO: 29)
                    |||||||||||||||||||||
3' mRNA majority    ATGACATAGTAGACGAGGACA (SEQ ID NO: 30)

Wobble position (~) perfect match, no wobble positions (i.e., acts as a
standard siRNA/shRNA with Watson-Crick pairing.

shRNA #4-2 (UR4-2 21nt DSir: 91.3 score)

3' IUPAC            YADYACTGTATCATCTGCYCC (SEQ ID NO:  8)

5' as RNA           UAGUACUGUAUCAUCUGCUCC (SEQ ID NO: 31)
                    ||~||||||||||||||||||
3' mRNA majority    ATTATGACATAGTAGACGAGG (SEQ ID NO: 32)

Wobble position (~) 3-> favored for no or beneficial effect shRNA #4-3 (UR4-3 21nt DSir: 84.4 score)

3' IUPAC            DYACTGTATCATCTGCYCCYG (SEQ ID NO:  9)

5' as RNA           GUACUGUAUCAUCUGCUCCUG (SEQ ID NO: 33)
                    ~||||||||||||||||||||
3' mRNA majority    TATGACATAGTAGACGAGGAC (SEQ ID NO: 34)

Wobble position (~) 1-> favored effect for activity reported
```

```
shRNA #4-4 (UR4-4 21nt DSir: 81.5 score)

3' IUPAC            ADYACTGTATCATCTGCYCCY  (SEQ ID NO: 10)

5' as RNA           AGUACUGUAUCAUCUGCUCCU  (SEQ ID NO: 35)
                    |~|||||||||||||||||||
3' mRNA majority    TTATGACATAGTAGACGAGGA  (SEQ ID NO: 36)

Wobble position (~) 2-> favored effect for activity reported
```

Example 2

Activity of shRNA Constructs

Figure 2:
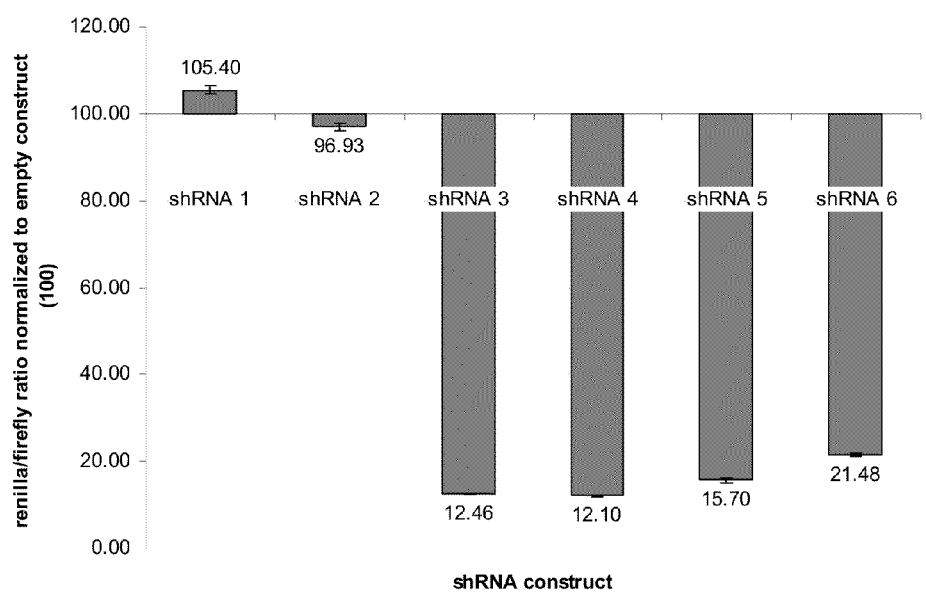
Figure 3:
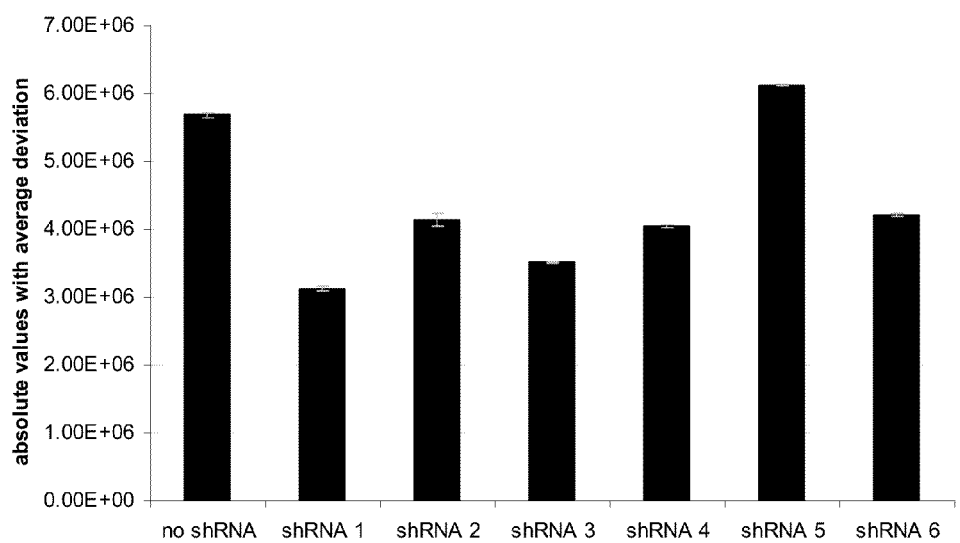

Region 4 Constructs Provide High Knockdown Activity Against a Luciferase Reporter Construct with NL4-3 Based Target Region From the HIV strain HXB2 fb a part of gag-pol coding region was cloned into psiCheck2.1 3' UTR with the primers gag-pol fw 5' atatCTCGAGCTTCAGAGCAGACCA-GAGCC (SEQ ID NO: 38) and gag-pol rev 5' tataGCGGC-CGCTCCCCACCTCAACAGATGTT (SEQ ID NO: 39) with restriction sites for XhoI and NotI. HEK293T were seeded at a density of 300.000 cells per well in 24 well plates and after 24 hours transfected with 300 ng psiCheck plasmid and 500 ng shRNA plasmid or empty plasmid without shRNA by delivery through Lipofectamine 2000. Two days later cells were harvested and dual luciferase assay (Promega) performed. While region 3 targeting shRNAs 3-2 and 3-3 (FIG. 2, shRNA 1 & shRNA 2) did not lead to significant knockdown, region 4 shRNAs (FIG. 2, shRNA 3-6) were all highly active with knockdown of the target gene by almost 90%. The firefly luciferase activity as transfection control showed equal delivery of the transfected plasmids and variation had no correlation with the knockdown values seen (FIG. 3).

Region 4 Constructs Prove Active Against an HIV Integrated Cell Line and a Full HIV Strain The HIfB cell line is generated by integration of the rev-deficient HXB2 fb HIV strain into HeLa cells. As rev changes the splicing pattern from short mRNAs to long mRNAs which encode the full virus genome and the mRNA encoding the nucleocapsid building protein gag-pol/p24 without rev there is no virus particle formation. Upon transfection of a rev expressing plasmids particle formation can be readily measured by detection of p24 via ELISA. 100.000 HIfB cells were seeded one day in advance in 24 wells before being transfected with 338 ng and 26 ng of shRNA constructs. 48 hours later supernatant was harvested, centrifuged at room temperature for 5 minutes at 300 rpm to remove possibly detached cells and p24 measured with the Alliance HIV-1 p24 antigen ELISA kit (Perkin Elmer, NEK050001 KT) according to manufacturer's protocol.

Figure 4:
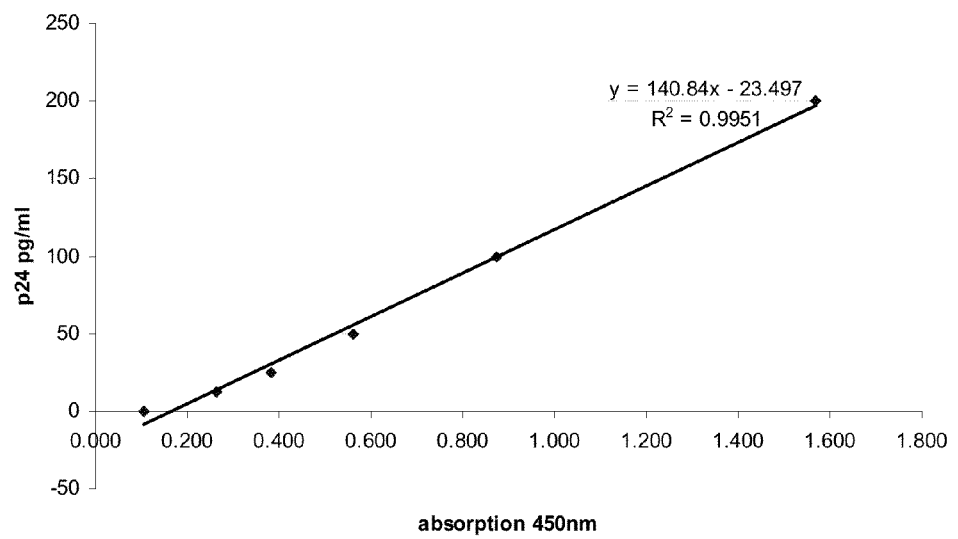
Figure 5:
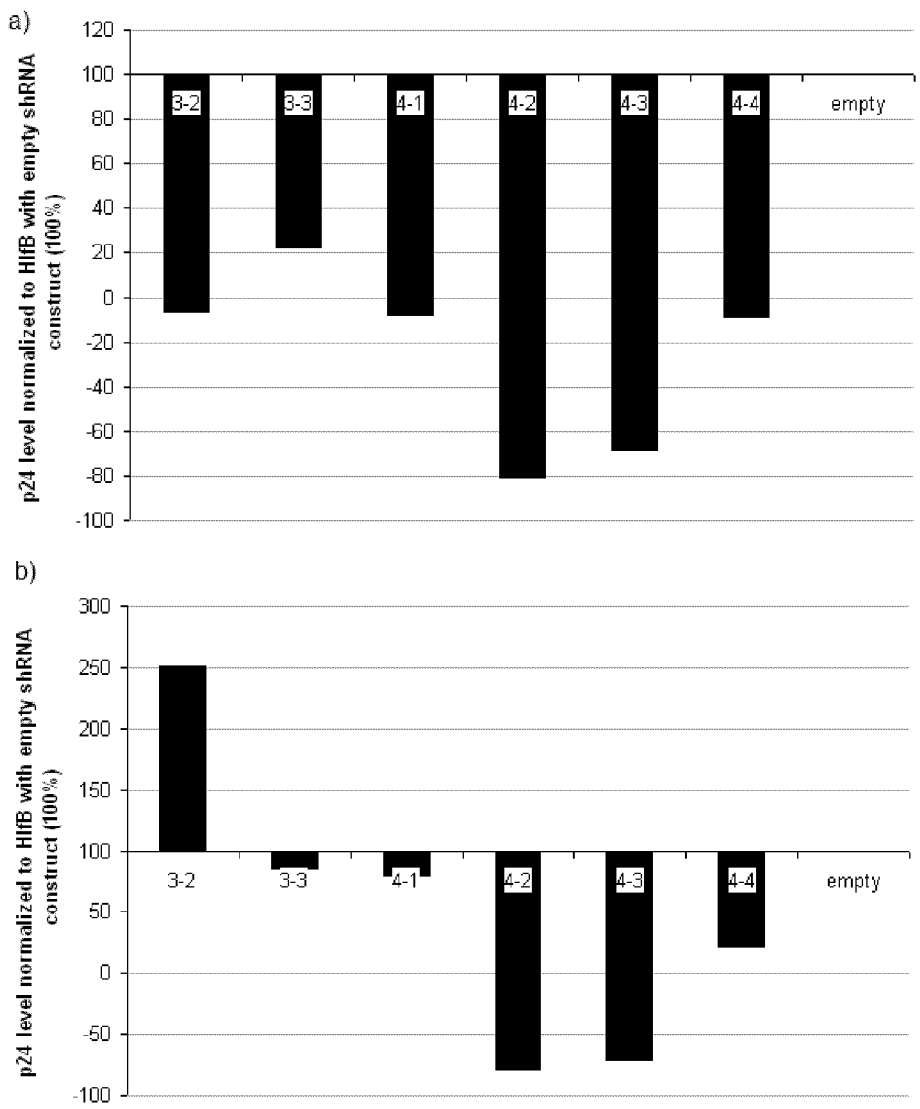

The assay was measured in a Victor 3 1420 (Perkin Elmer) at 450 nm & 490 nm. The standard curve for the assay was determined according to manufacturer's protocols and gave a very linear curve with an R(square) of 0.9951 (FIG. 4) at 450 nm wavelength. Strong knockdown was observed with region 4 targeting shRNAs again while region 3 targeting shRNAs showed an effect when 338 ng were transfected indicating a dose response effect (FIG. 5).

Figure 6:
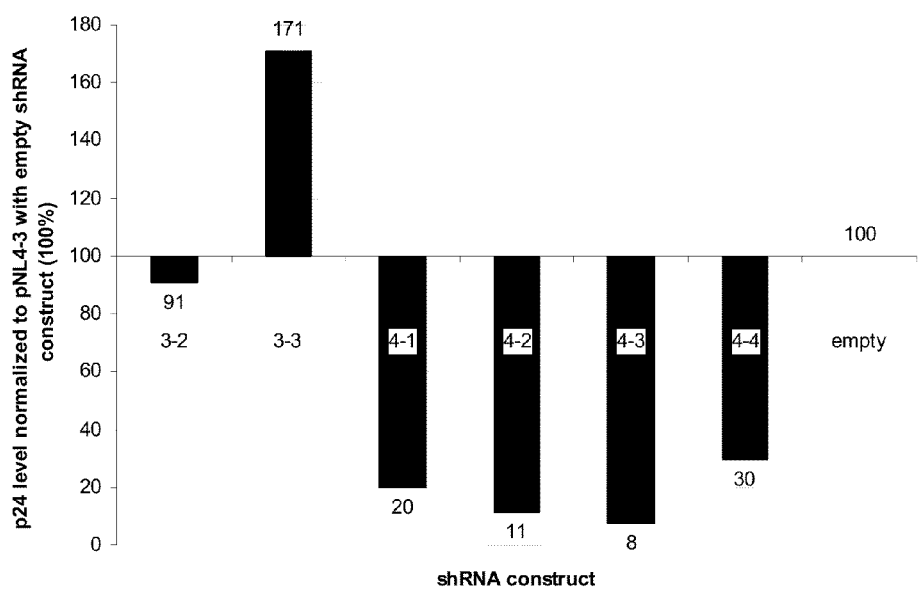

Since HIfB is a defective integrated HIV genome needing rev complementation and as it generates a very low p24 level (empty construct transfected gave only a bit over 5 pg p24/ml which is close to the assay detection limit the experiment was repeated with the full HIV strain NL4-3 which can be delivered as provirus encoded in the plasmid pNL4-3. We transfected 200 ng of pNL4-3 and 262 ng empty construct in each sample HEK293T (100.000 cells seeded in 24 well format one day prior transfection). In parallel 338 ng of shRNA or empty construct were transfected as well. 48 hours post transfection p24 levels were measured (same standard curve, FIG. 4). The p24 level of NL4-3 was much higher than HIfB and reached 142 pg p24/ml supernatant in the empty sample. Region 3 targeting shRNAs did not cause significant knockdown or up-regulation, while region 4 targeting shRNAs had a strong effect on p24 levels with a maximum knockdown level of 92% (FIG. 6).

A Virus Propagation Assay of HIV IIIB MuSTER Constructs Show Significant Activity in a Stably Transduced CEM-CCR5 Tcell Line CEM CCR5 cells (obtained from ATCC) were stably transduced with vectors expressing no shRNA, MuSTER shRNA, a conventional shRNA S1 with anti-HIV activity used in Clinical trials in the same background or expressed from the polymerase III U6 promoter. Transduction was determined by GFP expression from the same vector and promoter (except in the case of the U6 driven S1 sequence which was expressed externally of the GFP cassette). CEM cells were transduced with very low multiplier of transduction (MOI) to achieve transduction rates below 10% and thus in majority single copy integration. Cells were sorted for GFP expression and challenged with HIV IIIB virus for 24 hours, next day cells were washed three times to remove remaining virus particles and each 3-4 days until day 11 two third of the volume replaced with fresh media. On day 8, day 11 and d15 supernatant was collected and quantitatively analyzed for p24 expression (Alliance HIV-1 p24 antigen ELISA kit (Perkin Elmer, NEK050001KT) according to manufacturer's protocol) (FIG. 11).

Figure 7:
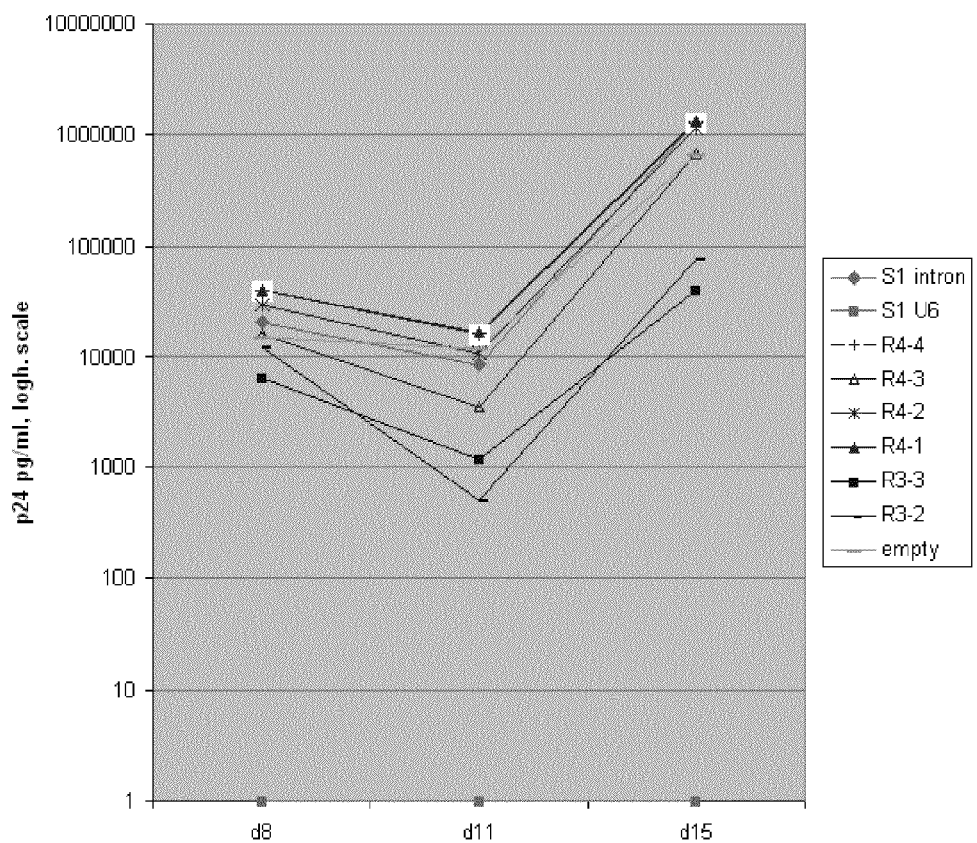

MuSTER designed shRNAs R3-2, R3-3 and R4-3 displayed significant activity against the HIV IIIB replication (FIG. 7). When the highly active U6 driven shRNA S1 was placed in the same background as the MuSTER shRNAs (polymerase II promoter CMV immediate early, which may yield a much lower dose of shRNA than U6) the effect of the conventional and highly active S1 shRNA fell below MuSTER designed R3-2, R3-3 and R4-3. Thus, the MuSTER design shRNAs can yield higher activity than the best known conventional shRNA in the same background.

Figure 8:
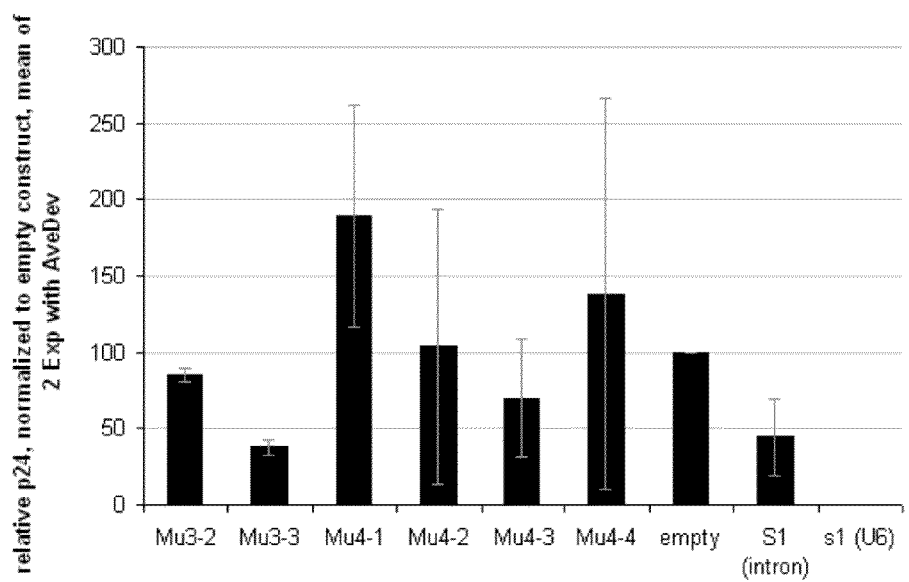

In addition, CEM cells were transduced with CCR5 using a lentiviral MuSTER expression constructs, single copy integration & challenged with HIV IIIB. On day 8, relative p24 expression was measured and normalized to an empty construct, mean of 2 Exp with AveDev. (FIG. 8).

Figure 9:
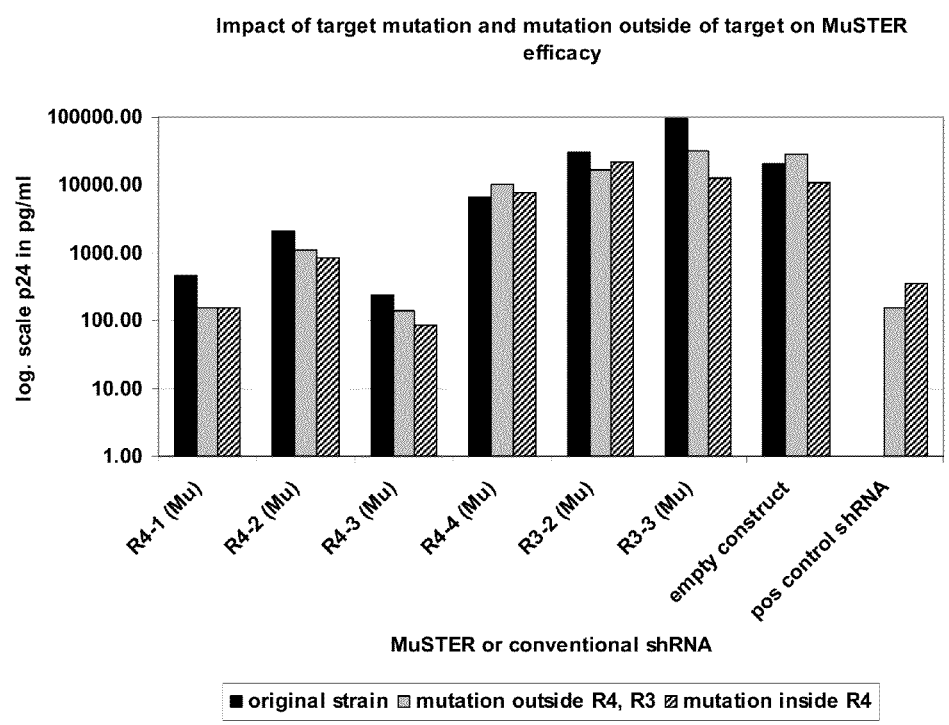
FIG. 9 shows the impact of target RNA sequence mutation inside and outside of the target RNA sequence region on the knockdown ability of MuSTER-designed shRNA constructs.

MuSTER Designed shRNAs Retain Activity when Target RNA Undergoes Mutation Inside and Outside of the Target Region Cells transfected with a plasmid expressing shRNA ID Nos. 3-2, 3-3, 4-1, 4-2, 4-3 and 4-4, an empty construct plasmid (no shRNA or MuSTER-designed shRNA) or a positive control plasmid (conventional shRNA that binds outside of the mutated region) were co-transfected with an original strain and two mutant strains of pNL4-3 HIV provirus. The mutant strains included 1978 nucleotides that span all MuSTER-designed viral RNA targets for two different HIV strains. In one mutant strain, the mutation occurred outside regions 3 and 4, and the second mutant strain included a mutation that occurs inside of region 4. 72 hours after transfection, a p24 assay was performed, the results of which showed that the MuSTER designed shRNAs do not lose their activity when the target viral RNA undergoes further mutation (FIG. 9). The positions and binding between the MuSTER designed shRNAs and the target sequence is shown in FIG. 10. Briefly, shRNA ID No. 4-1 (R4-1) binds region 4 (R4) in the original strain as well as the HIV in the mutant strain with the mutation occurring outside of R4 and regions 3 (R3) with Watson-Crick pairing; but binds the mutant strain with the mutation occurring within R4 with one non-Watson-Crick pair. shRNA ID No. 4-2 (R4-2) binds all three HIV strains within R4 with one non-Watson-Crick pair. shRNA ID No. 4-3 (R4-3) binds all three HIV strains within R4 with one non-Watson-Crick pair, but binds the mutant strain with the mutation occurring within R4 with one additional non-Watson-Crick pair. shRNA ID No. 4-4 (R4-4) binds all three HIV strains within R4 with one non-Watson-Crick pair (at a different position in the guide strand as compared to R4-3), but binds the mutant strain with the mutation occurring within R4 with one additional non-Watson-Crick pair. shRNA ID Nos. 3-2 and 3-3 (R3-2 and R-3-3) bind within R3 in the original strain with several non-Watson-Crick pairings (different positions of the guide strand between both), with no change to the target site in the mutant strains.

Discussion

In the experiments described in the Examples above, six shRNAs (shRNA ID Nos. 3-2, 3-3, 4-1, 4-2, 4-3, 4-4) were generated against 2 highly conserved regions in the HIV gag-pol coding sequence. These conserved regions were also found to have many naturally occurring mutants when analyzed against a database containing clinical isolates identified world wide. Therefore, the shRNAs were designed against artificial IUPAC sequences which take into account all known mutants using a MuSTER method described above. As such, these shRNAs should bind the target region despite mutation as they include non-Watson/Crick base pairing at the position of ambiguity.

While region 3 caused a knockdown effect against HIV strain HxB2 fb with very high shRNA dosage, region 4 targeting shRNAs yielded consistently high knockdown in both HxB2 and NL4-3 strains and the psiCheck reporter. This supports the design strategy since region 4 shRNAs already contains non-Watson/Crick pairing against both strains in case of shRNA ID Nos. 4-2, 4-3 and 4-4 while 4-1 comprises a conventional shRNA.

Conversely while region 3 targeting shRNAs show no effect in the HIV strains HxB2 and NL4-3 they demonstrate high activity in subsequent experiments with the HIV strain IIIB. The actual target regions in HIV IIIB, HxB2 and NL4-3 should be the same according to sequencing from AIDSrepository.org. But surrounding sequences differ thus folding of surrounding RNA sequences can limit access of si/shRNAs to the individual target sites. This escape mechanism has been shown previously for conventional shRNAs (Westerhout, Ooms et al. 2005) and can be overcome by the combinatorial expression of several si/shRNAs targeting different regions. Our approach proves that two different regions both have highly active shRNA of MuSTER design and can cover different HIV strains thus a combinatorial approach of both should cover even mutations that limit accessibility to a single target region.

Another possible explanation for the lower activity of region 4 targeting shRNAs in HIV IIIB would be that this strain not produced from a stable DNA template as is true for NL4-3 and HxB2 but it is produced in a virus propagation assay where virus is used to infect cells which produce fresh virus etc. So HIV IIIB is a pool of several varying sequences and it is not clear how far these might have deviated from the original deposited sequence. They could differ from NL4-3 in the target regions as well beyond the known mutations. This is less likely but can once more be overcome by combinatorial use of MuSTER designed si/shRNAs.

In conclusion, results from these investigations, which used three HIV strains (HxB2 fb, NL4-3 and IIIB), indicate that the MuSTER designed shRNA of both target regions may have high antiviral activity on their target region with the extend of this effect being impacted either by external sequence structuring or target region mutation. Therefore, in some embodiments, a single RNAi molecule may be used to suppress the expression of the target viral RNA sequence. In other embodiments, a combination of two or more RNAi molecules, each of which bind a different target viral RNA sequence, may be used to suppress the expression of two or more target viral RNA sequences, which would allow protection to be conferred while the virus mutates at least to some degree even outside of the target region.

Furthermore we tested the MuSTER design method against exotic non-clade B HIV-1 subtype sequences from databases. While these contain mutations in both target regions they are still leading to almost perfect pairing patterns with MuSTER which means the MuSTER shRNAs should retain activity. This confirms that the selected target sites are highly conserved. Experiments to test the activity of MuSTER against specifically mutated target sites have been demonstrated to not interfere with the shRNA activity and further experiments to test more mutations are under way.

Besides shRNAs expressed from templates inside the cells the design strategy can be employed as well for pre-synthesized siRNAs. In this case, the variety of possible modification is even larger like the introduction of inosine, selenium bases and modifications found in tRNA anti-codons. Furthermore, other pairings/mismatches besides Guanine-Uracil can be tested in certain positions to expand on possible/frequent mutations (Du, Thonberg et al. 2005; Nolen, Moe et al. 2005).

In some embodiments, the MuSTER design methods and strategy may also be used to predict target accessibility of the HIV strain and compare the results with the MuSTER target stretch selection and chose the precise target region based on MuSTER-compatibility as well as conservation of structure to retain accessibility. Using this strategy, it is possible that MuSTER designed RNAi molecules could be generated that no longer are designed to cover all strains with perfect pairing (Watson/Crick and non-Watson/Crick) but retain accessibility to the target sequence. Naturally occurring microRNA are active even in case of imperfect complementarity with the target as long as the seed sequence retains perfect pairing. Thus a slightly imperfect pairing beyond the capabilities of non-Watson/Crick pairing may still yield highly active sequences and the MuSTER approach is viable even in the case where an shRNA has fewer than 100% pairing with its target sequence (by Watson Crick or non-Watson Crick pairing). A combinatorial construct of several MuSTER-designed shRNA which do not necessarily cover all strains could close the gap to again cover all or the majority of randomly occurring HIV mutants.

REFERENCES

The references, patents and published patent applications listed below, and all references cited in the specification above are hereby incorporated by reference in their entirety, as if fully set forth herein.

Anderson, A. C., R. H. O'Neil, et al. (1999). "Crystal structure of a brominated RNA helix with four mismatched base pairs: An investigation into RNA conformational variability." *Biochemistry* 38(39): 12577-12585.

Bao, Y., P. Bolotov, et al. (2008). "The influenza virus resource at the National Center for Biotechnology Information." *J Virol* 82(2): 596-601.

Du, G., J. Yonekubo, et al. (2006). "Design of expression vectors for RNA interference based on miRNAs and RNA splicing." *FEBS J* 273(23): 5421-5427.

Du, Q., H. Thonberg, et al. (2005). "A systematic analysis of the silencing effects of an active siRNA at all single-nucleotide mismatched target sites." *Nucleic Acids Res* 33(5): 1671-1677.

Holen, T., S. E. Moe, et al. (2005). "Tolerated wobble mutations in siRNAs decrease specificity, but can enhance activity in vivo." *Nucleic Acids Res* 33(15): 4704-4710.

Joseph, T. T. and R. Osman (2012). "Convergent transmission of RNAi guide-target mismatch information across Argonaute internal allosteric network." *PLoS Comput Biol* 8(9): e1002693.

Sun, H., J. Sheng, et al. (2012). "Novel RNA base pair with higher specificity using single selenium atom." *Nucleic Acids Res*.

Vendeix, F. A., F. V. t. Murphy, et al. (2012). "Human tRNA (Lys3)(UUU) is pre-structured by natural modifications for cognate and wobble codon binding through keto-enol tautomerism." *J Mol Biol* 416(4): 467-485.

Westerhout, E. M., M. Ooms, et al. (2005). "HIV-1 can escape from RNA interference by evolving an alternative structure in its RNA genome." *Nucleic Acids Res* 33(2): 796-804.

---

What is claimed is:

1. An RNA interference (RNAi) molecule comprising:
a synthesized inhibitory RNA sequence comprising a sequence

```
                              (SEQ ID NO: 13)
       GTACTGTATCATCTGCTCCTG
``` which binds a target pathologic RNA sequence, via at least one non-Watson Crick paired base, wherein the target pathologic RNA sequence is a target viral RNA sequence derived from a human immunodeficiency HIV virus.

2. The RNAi molecule of claim 1, wherein the target viral RNA sequence comprises an IUPAC sequence of YURGAY-ACRGGRGCAGAUGAUACAGUR (SEQ ID NO:2).

3. The RNAi molecule of claim 1, wherein the IUPAC sequence binds the target pathologic RNA sequence via at least one non-Watson Crick paired base which occurs at a base identified as D or Y.

\* \* \* \* \*

SEQUENCE LISTING

```
<160> NUMBER OF SEQ ID NOS: 42

<210> SEQ ID NO 1
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 1
urycaruaya uggaygayyu ruaugurgg                                             29

<210> SEQ ID NO 2
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 2
yurgayacrg grgcagauga uacagur                                               27

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
yarrtcrtcc atrtaytgry a                                                     21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tayarrtcrt ccatrtaytg r                                                     21

<210> SEQ ID NO 5
<211> LENGTH: 21
```

```
<212> TYPE: DNA
<213> ORGANISM: Artificial Sequence
<220> FEATURE:
<223> OTHER INFORMATION: Synthetic oligonucleotide

<400> SEQUENCE: 5
taggtcgtcc atgtattggt a                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
tataggtcgt ccatgtattg g                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
yactgtatca tctgcyccyg t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
yadyactgta tcatctgcyc c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
dyactgtatc atctgcyccy g                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
adyactgtat catctgcycc y                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
```
tactgtatca tctgctcctg t                                                      21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
tagtactgta tcatctgctc c                                                      21

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
gtactgtatc atctgctcct g                                                      21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
agtactgtat catctgctcc t                                                      21

<210> SEQ ID NO 15
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 15
agcgatacca atacatggac gacctatagt gaagccacag atgtataggt cgtccatgta           60
ttggtagtgc c                                                                 71

<210> SEQ ID NO 16
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 16
agcggccaat acatggacga cctatatagt gaagccacag atgtatatag gtcgtccatg           60
tattggttgc c                                                                 71

<210> SEQ ID NO 17
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 17
agcgaacagg agcagatgat acagtatagt gaagccacag atgtatactg tatcatctgc           60
tcctgtgtgc c                                                                 71

```
<210> SEQ ID NO 18
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 18
agcggggagc agatgataca gtactatagt gaagccacag atgtatagta ctgtatcatc      60
tgctccttgc c                                                          71

<210> SEQ ID NO 19
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 19
agcggcagga gcagatgata cagtactagt gaagccacag atgtagtact gtatcatctg      60
ctcctgttgc c                                                          71

<210> SEQ ID NO 20
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 20
agcgaaggag cagatgatac agtacttagt gaagccacag atgtaagtac tgtatcatct      60
gctcctgtgc c                                                          71

<210> SEQ ID NO 21
<211> LENGTH: 32
<212> TYPE: RNA
<213> ORGANISM: Artificial Sequence
<220> FEATURE:
<223> OTHER INFORMATION: Synthetic oligonucleotide

<400> SEQUENCE: 21
arruggagra aryurgurga yuuyagrgar yu                                   32

<210> SEQ ID NO 22
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 22
raugayauca caraaryurg urggraar                                        28

<210> SEQ ID NO 23
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 23
aararrggyu gyurgaarug ur                                              22
```

<210> SEQ ID NO 24
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 24
rrgggarrra gaurrgugcr ag                                              22

<210> SEQ ID NO 25
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 25
uaggucgucc auguauuggu a                                               21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
gtttagtagg tacataacta t                                               21

<210> SEQ ID NO 27
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 27
uauaggucgu ccauguauug g                                               21

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 28
atgtttagta ggtacataac t                                               21

<210> SEQ ID NO 29
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 29
uacuguauca ucugcuccug u                                               21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide -continued

```
<400> SEQUENCE: 30
atgacatagt agacgaggac a                                              21

<210> SEQ ID NO 31
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 31
uaguacugua ucaucugcuc c                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
attatgacat agtagacgag g                                              21

<210> SEQ ID NO 33
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 33
guacuguauc aucugcuccu g                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
tatgacatag tagacgagga c                                              21

<210> SEQ ID NO 35
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 35
aguacuguau caucugcucc u                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
ttatgacata gtagacgagg a                                              21

<210> SEQ ID NO 37
```

```
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 37
ytrgayacrg grgcagatga tacagtr                                         27

<210> SEQ ID NO 38
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 38
atatctcgag cttcagagca gaccagagcc                                      30

<210> SEQ ID NO 39
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 39
tatagcggcc gctcccacc tcaacagatg tt                                    32

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 40
taatactgta tcatctgctc ctgt                                            24

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
taatactgta tcatctgctc cggt                                            24

<210> SEQ ID NO 42
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 42
cctacataca aatcatccat gtattgata                                       29
```